United States Patent [19]

Cadmus

[11] 4,410,625

[45] Oct. 18, 1983

[54] SALT-TOLERANT MICROBIAL XANTHANASE AND METHOD OF PRODUCING SAME

[75] Inventor: Martin C. Cadmus, Peoria, Ill.

[73] Assignee: The United States of America as represented by the Secretary of Agriculture, Washington, D.C.

[21] Appl. No.: 345,512

[22] Filed: Feb. 4, 1982

[51] Int. Cl.$^3$ ............................................. C12P 39/00
[52] U.S. Cl. ..................................... 435/42; 435/104; 435/200; 435/274; 435/829; 435/830; 435/840; 435/850; 435/859; 435/910
[58] Field of Search ................................ 435/829–830, 435/42, 840, 104, 253, 281, 274, 832, 850, 859, 910

[56] References Cited

U.S. PATENT DOCUMENTS 2,742,398  4/1956  ZoBell ............................. 435/42 X

OTHER PUBLICATIONS

Cripps et al., "Xanthanase Enzyme", Chemical Abstracts, vol. 95, p. 258, Abstract No. 146157q.
M. Rinaudo et al., "Enzymic Hydrolysis of the Bacterial Polysaccharide Xanthan by Cellulase," Chem. Abstr. 92: 176420a, (1980).

Primary Examiner—R. B. Penland
Attorney, Agent, or Firm—M. Howard Silverstein; David G. McConnell; Curtis P. Ribando

[57] ABSTRACT

A novel Bacillus isolated from the soil is unique in its capacity to produce xanthanase, and is especially productive of the enzyme when cultured in the presence of other soil organisms. Both crude and purified xanthanases recovered from the fermentation broth effectively degrade xanthan gum. Moreover, tolerance of the Bacillus to sodium chloride levels as high as about 4%, render it useful for the in situ degradation of the heteropolysaccharide in petroleum recovery fluids and other thickened industrial brines.

8 Claims, No Drawings

SALT-TOLERANT MICROBIAL XANTHANASE AND METHOD OF PRODUCING SAME

BACKGROUND OF THE INVENTION

1. Field of the Invention

Xanthan gum is a heteropolysaccharide produced as a fermentation product by *Xanthomonas campestris*, a microorganism causing vascular disease of cabbages, cauliflower, and rutabagas. Its structure consists of a linear backbone of $\beta$-(1→4)-linked D-glucose resides (linked as in cellulose), which has three-unit-long side chains appended on alternate residues. D-Mannose residues directly appended to the backbone bear O-acetyl substituents on the C-6 position. Pyruvic acetal, i.e., 4,6-O-(1-carboxyethylidene), substituents are on the terminal D-mannosyl residues of some of these side chains, their frequency of occurrence depending on the bacterial strain and fermentation conditions.

Xanthan gum has condiderable industrial significance and a vast variety of applications as summarized by A. Jeanes in "Applications of Extracellular Microbial Polysaccharide-Polyelectrolytes: Review of Literature, Including Patents," J. Polym. Sci., Polym. Symp. No. 45, pp. 216–221 (1974). The stability of its rheological properties under diverse chemical conditions accounts in part for its versatility. For example, the gum is an effective brine thickener for use in drilling mud compositions and also in the secondary and tertiary recovery of petroleum. A detailed description of its role in oil recovery is given by Wernau in U.S. Pat. No. 4,119,546. With the potential for use of large quantities in this and other fields, there has been some concern as to its effect on the environment. We have observed that the gum is unaffected after exposure for a year or more to laboratory air or for 10 years when stored in nonsterile tightly closed containers. Even when in contact with high concentrations of soil organisms, the heteropolysaccharide may remain stable for as long as a month. Faced with these observations suggesting that xanthan-degrading organisms are not abundant in nature, this invention relates to the identification and isolation of a culture effective for degrading the gum.

2. Description of the Prior Art

While the literature is replete with reports on the production, characterization, properties, and applications of xanthan gum, there is a paucity of information on its biochemical degradation. M. Rinaudo et al. [Chem. Abstr. 92: 176420a (1980)] investigated the mechanism of enzymic hydrolysis by a cellulase. In salt-free solution, a random breakdown of the main chain was observed when the polysaccharide was in the unordered conformation. However, there was no hydrolysis of the more commonly occurring, ordered helical conformation.

SUMMARY OF THE INVENTION

I have now discovered a xanthanase-producing bacterium which demonstrates the capacity to elaborate salt-tolerant extracellular enzymes that degrade xanthan gum in both its ordered and unordered conformations. This organism possesses the taxonomic characteristics of Bacillus and has been deposited in the Agricultural Research Service Culture Collection in Peoria, Ill., under the Accession No. NRRL B-4529. I have additionally discovered that the somewhat limited enzyme production in pure culture is greatly enhanced when this strain is incubated with at least one other soil organism. Also, the resultant mixed culture is more stable over extended periods of storage.

In accordance with this discovery, it is an object of the invention to provide a means for biochemically degrading xanthan gum.

It is also an object of the invention to produce relatively high yields of xanthanase by a commercially feasible fermentation process.

Another object of the invention is to produce a xanthanase which is tolerant to the diverse conditions of xanthan utilization.

Other objects and advantages of this invention will become readily apparent from the ensuing description.

DETAILED DESCRIPTION OF THE INVENTION

The xanthanase producer of this invention was originally isolated from a mixture of soil and tree stump decay. Taxonomically, B-4529 is similar, but not identical to, *Bacillus lentus* as apparent from the comparison in Table I, below. *B. lentus* as well as several other Bacillus species specifically assayed for xanthanase activity all fail to produce the enzyme.

The xanthanase production by B-4529 will be increased by the presence of any other microorganism or combination of microorganisms which enhances the growth of B-4529 when in mixed culture therewith on a suitable xanthan-containing medium. This includes most species of soil genera. Illustrative thereof, without limitation thereto, are Arthrobacter, Alcaligenes, Agrobacterium, Bacillus, Brevibacterium, Alavobacterium, Micrococcus, and Xanthomonas. The conglomerate of unidentified strains present in the original soil sample source of B-4529 elicits in mixed culture at least a doubling of the xanthanase elaboration over that of the pure culture. The same is true of individual isolated strains from the sample, particularly that which has been deposited in the ARS Culture Collection under Accession No. B-14010. The enhanced enzyme production in mixed culture is indicative of a commensalistic or symbiotic relationship accruing to the benefit of the xanthanase producer.

Whether the fermentation contemplated by this invention is for the purpose of direct degradation of xanthan gum or for the receovery of xanthanases for use as stock reagents, the polysaccharide is an essential component of the medium. This suggests that the xanthan degradation products are assimilated by the growing Bacillus. Other nutrients necessary for growth include ammonium sulfate, potassium phosphate, and a mineral mixture. Suitable media formulations will typically contain about 1–3 g./l. purified xanthan, about 0.25–1 g./l. ammonium sulfate, 0–2 g./l. yeast extract, about 0.2 g./l. tryptone, about 0.5–2 g./l. monobasic potassium phosphate, about 0.5–1 g./l. diabasic potassium phosphate, and about 1–3 ml. of a standard mineral solution.

TABLE I

| Property[a] | B. lentus | NRRL B-4529 |
| --- | --- | --- |
| Rods: | | |
| Width, $\mu$ | 0.6–0.9 | 0.75–1.0 |
| Length, $\mu$ | 1.2–4 | 2.0–3.0 |
| Gram reaction | + | + |
| Spores: | | |
| Ellipsoidal | + | + |
| Round | − | − |

TABLE I-continued

| Property[a] | B. lentus | NRRL B-4529 |
|---|---|---|
| Swelling the sporangium | − | − |
| Motility | + | + |
| Catalase | + | + |
| Anaerobic growth | − | − |
| V-P reaction | − | − (no growth) |
| pH in V-P broth | 6.4 | 6.2–6.3 |
| Temperature of growth, °C.: | | |
| Maximum | 35 | 37 |
| Minimum | 10 | 20[b] |
| Growth in: | | |
| Media, pH 5.7 | − | − |
| NaCl (4% in xanthan broth) | n | + |
| NaCl (5%) | + | n |
| NaCl (7% in nutrient broth) | n | − |
| Acid from: | | |
| Glucose | + | + |
| Arabinose | m | −[c] |
| Xylose | m | −[c] |
| Mannitol | + | −[c] |
| Hydrolysis of starch | + | + |
| Use of citrate | − | − |
| Reduction of NO$_3$ to NO$_2$ | − | − |
| Formation of indole | − | − |
| Deamination of phenylalanine | m | − |
| Decomposition of: | | |
| Casein | − | − |
| Tyrosine | − | − |

[a]Determined by methods of R. E. Gordon et al., Agricultural Handbook No. 427. Percentage of strains with indicated characteristic: +, 85–100; m, 50–84; −, 0–14; n, undetermined.
[b]Minimum temperature tested.
[c]Characterization questionable as a result of negligible growth.

While sodium chloride is not necessary for growth, B-4529 is tolerant of levels thereof in the medium as high as at least about 4.0%. In order for the organism to maintain its salt tolerance, it is recommended that all buildup media contain similarly high NaCl levels. The preferred medium in terms of optimum xanthanase production is set forth in Table II, below.

TABLE II

|  | % w/v |
|---|---|
| xanthan | 0.2 |
| (NH$_4$)$_2$SO$_4$ | 0.05 |
| tryptone | 0.18 |
| KH$_2$PO$_4$ | 0.15 |
| K$_2$HPO$_4$ | 0.07 |
| MgSO$_4$.7H$_2$O | 0.04 |
| MnSO$_4$.4H$_2$O | 0.002 |
| NaCl | 4.0 |
| water | 95.308 |
|  | 100.000 |

The incubation is preferably conducted in the temperature range of 25°–32° C. and at an initial pH in the range of about 5.5 to about 7.0, and more preferably at a temperature of 30° C. and a pH of 6.4. Under these conditions, the xanthan in a production batch is completely fermented in 3–4 days by which time the pH has typically risen between about 0.1 to 1.0 pH units. Below 25° C., the fermentation rate is noticeably retarded and above 32° C. the xanthanase yield diminishes. It is envisioned that pH's as low as about 5.0 can be employed without significant effect on the production or stability of the xanthanase. As the pH approaches 7.5, the xanthanase yield rapidly declines. The fermentation is aerobic and the requisite air flow rate will depend upon factors such as vessel capacity and design, batch size, and the specific culture mixture. Guided by growth rates and xanthanase yields, the optimum rate can be readily determined by the skilled artisan. When the primary purpose of the fermentation is the in situ degradation of the xanthan gum, without recovery of the enzyme, optimization of the culture conditions is not of paramount consequence. However, when the enzyme yield is to be maximized, it is necessary to control the conditions within the aforementioned ranges.

A crude enzyme preparation can be isolated from the fermentation broth by removal of cells such as by centrifugation or filtration. If desired, the enzyme in the supernatant can then be concentrated by filtration or other conventional means. One or more passes of the crude concentrate on an ion exchange chromatographic column is effective for obtaining a substantially pure product. While the specific activity of the crude concentrate will typically be on the order of about 1000–3000 enzyme units/mg., the ion exchange treatment will result in specific activities of at least about 15,000 units/mg. Activities of preparations considered to be substantially pure for purposes of the invention will range between about 25,000 and 35,000 units/mg. An enzyme unit is defined as the number of milligrams per 100 milliliters of reducing sugar (calculated as D-mannose) liberated per milliliter of enzyme from xanthan in 1 hour at 42° C. and at pH 5.4.

Both crude and purified enzyme preparations are readily stored at low temperatures as solutions buffered in the range of pH 6.0 to 7.5. For instance, at 4° C. there is no noticeable loss of activity over a 3-month period. At 38°–42° C., the buffered solutions may lose up to 10% of their activity over a 30-minute interval, but even this loss can be completely inhibited by the presence of as little as 0.25% xanthan substrate. Frozen and lyophilized preparations are also stable for extended periods.

The xanthanase of this invention exhibits activity within the pH range of about 4 to 7, and especially between pH 5 and 6. On a salt-free xanthan substrate, optimum conditions are pH 5.4 and 48° C., whereas in the presence of 0.1 M NaCl the preferred temperature is 42° C. The rate of enzymic degradation of xanthan gum is also related to the gum's concentration in aqueous solution, with levels of less than about 1% being preferred.

Without desiring to be bound to any particular theory of operation, it is believed that the xanthanase is a carbohydrase mixture that attacks all the side-chain linkages in the xanthan polysaccharide, including the one involving (1→3)-linkage of acetylated mannose to the glucosidic backbone. Under suitable conditions, the side chains are completely removed and degraded, thereby liberating approximately half of the theoretical sugar content of the gum. This degree of degradation is sufficient to negate virtually all thickening imparted to solutions of the gum. The β-(1→4)-linked glucosidic backbone remains intact, indicating the absence of an endocellulase type of activity.

In addition to increasing the rate of biodegradation, several potential uses for xanthanases can be envisioned. Isolated enzymes can alter xanthan and related polysaccharide structures for subsequent chemical or biological modifications. The enzymes might also be used to confirm existing xanthan structures and possibly to show a certain specificity for related polysaccharides produced by different species of microorganisms. Xanthanases may also be useful in tailoring the viscosity of suspensions for a particular use, such as thinning suspensions prior to injection into underground oil-bearing formations.

The following examples are intended only to further illustrate the invention and are not intended to limit the scope of the invention which is defined by the claims. Descriptions of the media referred to in the examples are set forth in Table III, below.

EXAMPLE 1

A mixed culture of unknown organisms designated 14 M was obtained from a soil sample collected from inside a decaying tree trunk in Iowa City, Iowa. Upon incubation on 20-ml. portions of broth medium A and broth Medium A+NaCl in rotary flasks at 30° C. for a month, 14 M assayed positive for xanthanase activity.

TABLE III

| Nutrient | Broth medium A, % w/v | Broth medium B, % w/v | Broth medium C, % w/v | KGM[b] medium, % w/v |
|---|---|---|---|---|
| Xanthan | 0.3 | 0.25 | 0.15 | 0.1 |
| Yeast extract | 0.02 | 0.08 | 0.08 | 0.08 |
| Tryptone | 0.02 | 0.04 | 0.04 | 0.04 |
| Peptone | 0.02 | — | — | — |
| D-Mannose | — | — | — | 0.1 |
| D-Glucose | — | — | — | 0.1 |
| Agar | — | — | — | 1.8 |
| $(NH_4)_2SO_4$ | 0.05 | 0.05 | 0.05 | 0.05 |
| $KH_2PO_4$ | 0.05 | 0.15 | 0.15 | 0.15 |
| $K_2HPO_4$ | 0.05 | 0.07 | 0.07 | 0.07 |
| NaCl | — | 4.0 | 4.0 | — |
| Salt solution[a] (% v/v) | 0.25 | 0.5 | 0.5 | 0.25 |
| pH | — | 6.4 | 6.4 | 6.4 |

[a]Speakman's salt solution B:
4.0% w/v $MgSO_4.7H_2O$
0.2% w/v $MnSO_4.4H_2O$
0.2% NaCl
0.2% $Fe(SO_4)_3.7H_2O$
[b]KGM = "Kelzan" - glucose-mannose medium.

An effort to isolate the xanthanase producer was begun by repeatedly transferring the mixed culture to fresh broth medium B at closer and closer intervals until activity was apparent in 24 hours with a 5% inoculum at 28° C. Sets of three plates containing "Kelzan"-glucose-mannose (KGM) media were serially streaked every 3 days from 24-hour fresh culture. After 3 days, individual colonies were selected and incubated on KGM slants for 48 hours. Flasks of medium broth B were inoculated from the slants for the purpose of assaying the isolate activity by monitoring the viscosity over approximately a 1-week period. Of the 97 isolates tested on the first three sets of plates, all were negative. In the fourth set of plates one of 34 isolates assayed positive. That one was taken from a colony characterized by a gray-translucent mucoid appearance and was labeled strain 11. Upon deposit in the ARS Culture Collection, this strain was designated Bacillus sp. NRRL B-4529.

EXAMPLE 2

A. Of the several xanthanase negative strains isolated from the mixed culture 14 M by the procedure of Example 1, two yellow colonies which visually appeared to be the same were designated as strains 3 and 17. Strain 17 was characterized taxonomically as shown in Table IV below and was deposited in the ARS Culture Collection under the Accession No. NRRL B-14010.

B. For the purpose of comparing the xanthanase activity of strain B-4529 in pure culture with that of B-4529 in combination with each of strains 3 and 17 in mixed culture, the following experiment was conducted. Three 50-ml. flasks were each prepared with 12 ml. of broth medium C.

TABLE IV

| Property[a,b] | NRRL B-14010 |
|---|---|
| Rods: | |
| Width, μ | 0.3–0.5 |
| Length, μ | 0.8–1.2 |
| Gram reaction | — |
| Motility | not always seen |
| Catalase | + |
| Esculin test | + |
| Xanthanase activity in xanthan + 1% NaCl | — |
| Growth supported without carbohydrate in medium | + |
| Growth in NaCl (4%) | + |
| Acid from glucose | + (no gas) |
| Formation of indole | — |
| Decomposition of: | |
| Casein | — |
| Gelatin | + |
| Tentative identification: | |
| Flavobacterium marinum | |
| Flavobacterium lutescens | |
| Flavobacterium harrisonii | |

[a]Determined by methods of R. E. Gorden et al., Agricultural Handbook No. 427.
[b]The Bacillus identification tests used above were employed in conjunction with Bergey's Manual for Tentative Indentification.

Each flask was then inoculated with the appropriate strain or strains taken from a 1–2 day inoculum which in turn had been inoculated from a 2–5 day agar slant. After incubating for 4 days on a rotary shaker at 200 r.p.m. and 28° C., the whole culture broth was harvested and centrifuged to remove the cells. The crude cell-free broth was assayed for xanthanase activity in 5 ml. of an assay mixture containing:
0.05% w/v xanthan
0.2% w/v Speakman's salt solution B
0.05 M NaOAc (pH 5.4)
1.0 ml. crude cell-free broth
4.0 ml. distilled water
The mixture was shaken in a tube, then placed in a 40° C. water bath for 15 minutes. The results are set forth in Table V below.

TABLE V

| Culture | Activity (enzyme units/ml.[a]) |
|---|---|
| B-4529 | 20 |
| B-4529 + strain 3 | 102 |
| B-4529 + strain 17 | 106 |

[a]Enzyme unit = mg./100 ml. of reducing sugar calculated as D-mannose liberated per ml. of broth in 1 hour at 42° C. and pH 5.4.

EXAMPLE 3

For the purpose of comparing the xanthanase activity of strain B-4529 in pure culture with that of B-4529 in combination with each of several randomly selected known soil organisms in mixed culture, the following experiment was conducted. KGM agar slants were inoculated from stock cultures of the organisms and after 4 days the cultures were paired together on fresh KGM agar slants. After 5 days the mixed cultures and the control were transferred to 50-ml. flasks containing 12 ml. of broth medium B and incubated on a rotary shaker at 200 r.p.m. and 29°–30° C. for 5 days. These cultures were finally transferred to 300-ml. flasks, each containing 50 ml. of broth medium B, and were incubated at 29°–30° C. on a rotary shaker at 200 r.p.m. for an additional 4 days. After visually evaluating the broth for xanthanase activity by viscosity reduction, the broth was harvested and centrifuged to remove the cells. The crude cell-free broth was then assayed for xanthanase activity by the procedure of Example 2 except that the substrate solution contained 0.1% w/v xanthan and was incubated at 37° C. It is apparent from the results reported in Table VI below that the activity of B-4529 is generally enhanced in mixed culture with other soil organisms, the exception being *Achromobacter xylosoxidans* NRRL B-4082. It is expected that after a few subcultures, most of the mixed cultures would yield an enzyme activity comparing favorably with that produced by B-4529+strain 17.

EXAMPLE 4

The original mixed culture 14 M was taken from a stock KGM slant and transferred to a fresh KGM slant for 2 days, and then transferred to a 300-ml. flask containing 75 ml. of broth medium C. After 3 days, 1 ml. of this broth was used to inoculate 20 ml. of fresh broth in 50-ml. flasks. The fresh broth was the same as that used for the inoculum except that the initial pH was adjusted to various levels. The results after 72 hours are set forth in Table VII, below.

EXAMPLE 5

The effect of medium composition on xanthanase production was determined by varying the nutrient levels in the following series of fermentations. A mixed culture of B-4529 and strain 17 maintained on cold-stored broth was serially transferred in the course of 6 days through four inoculum flasks containing broth medium B. On the seventh day, 12 ml. of test media in 50-ml. flasks were inoculated with 0.5 ml. of inoculum from the fourth serial flask. Duplicate media at each nutrient combination enabled harvesting on both the third and fourth days. All basal media contained 0.15% w/v KH$_2$PO$_4$, 0.07% w/v K$_2$HPO$_4$, and 4.0% w/v NaCl. In each case the initial pH was 6.4 and incubation was at 30° C. The results are reported in Table VIII, below.

TABLE VI

| Test | Culture Xanthanase strain | Non-xanthanase soil organism (NRRL Accession No.) | Broth evaluation[a] 48 hr. | 5 da. | Activity (enzyme units/ml.)[b] |
|---|---|---|---|---|---|
| A | B-4529 | — | — | +++ | 43 |
| B | B-4529 | 17 (B-14010) | ++++ | ++++ | 114 |
| C | B-4529 | *Agrobacterium radiobacter* (B-164) | +++ | +++ | 50 |
| D | B-4529 | *Alcaligenes faecalis* (B-170) | ++ | +++ | 62 |
| E | B-4529 | *Xanthomonas campestris* (B-1459) | ++++ | ++++ | 61 |
| F | B-4529 | *Arthrobacter viscosus* (B-1973) | +++ | +++ | 55 |
| G | B-4529 | *Flavobacterium aquatile* (B-2157) | + | ++++ | 65 |
| H | B-4529 | *Micrococcus luteus* (B-2975) | +++ | +++ | 58 |
| I | B-4529 | *Arthrobacter simplex* (B-3157) | ++ | ++++ | 98 |
| J | B-4529 | *Arthrobacter globiformis* (B-3159) | + | ++++ | 58 |
| K | B-4529 | *Achromobacter xylosoxidans* (B-4082) | ++ | +++ | 26 |
| L | B-4529 | *Brevibacterium linens* (B-4210) | + | ++++ | 90 |

[a]Based on visual observation of the extent of viscosity reduction: − = no reduction; ++++ = total reduction.
[b]Enzyme unit = mg./100 ml. of reducing sugar (calculated as D-mannose) liberated per ml. broth in 1 hour at 42° C. and pH 5.4.

TABLE VII

| Test | Initial pH | Final pH | Activity (enzyme units/ml.)[a] |
|---|---|---|---|
| A | 5.5 | 5.90 | 18.8 |
| B | 6.0 | 6.10 | 18.8 |
| C | 6.4 | 6.20 | 20.4 |
| D | 7.0 | 6.85 | 19.6 |

TABLE VII-continued

| Test | Initial pH | Final pH | Activity (enzyme units/ml.)[a] |
|---|---|---|---|
| E | 7.5 | 8.10 | 3.6 |

[a]Enzyme unit = mg./100 ml. reducing sugar (calculated as D-mannose) liberated per ml. broth in 1 hour at 42° C. and pH 5.4.

TABLE VIII

| Test | Xanthan, % w/v | (NH$_4$)$_2$SO$_4$, % w/v | Yeast extract, % w/v | Tryptone, % w/v | Salt solution[a], % v/v | Activity (enzyme units/ml.)[b] 3 da. | 4 da. |
|---|---|---|---|---|---|---|---|
| A | 0.20 | 0.05 | 0.08 | 0.04 | 0.50 | 150 | 164 |
| B | 0.25 | 0.05 | 0.08 | 0.04 | 0.50 | 186 | 190 |
| C | 0.30 | 0.05 | 0.08 | 0.04 | 0.50 | 194 | 210 |
| D | 0.20 | 0.025 | 0.08 | 0.04 | 0.50 | 200 | 136 |
| E | 0.20 | 0.075 | 0.08 | 0.04 | 0.50 | 180 | 160 |
| F | 0.20 | 0.10 | 0.08 | 0.04 | 0.50 | 180 | 168 |
| G | 0.20 | 0.05 | 0.12 | 0 | 0.50 | 172 | 160 |
| H | 0.20 | 0.05 | 0 | 0.12 | 0.50 | 222 | 212 |
| I | 0.20 | 0.05 | 0 | 0.18 | 0.50 | 232 | 214 |
| J | 0.20 | 0.05 | 0.04 | 0.08 | 0.50 | 204 | 162 |
| K | 0.20 | 0.05 | 0.06 | 0.12 | 0.50 | 200 | 164 |
| L | 0.20 | 0.05 | 0.08 | 0.04 | 1.0 | 198 | 166 |

[a]4.0% w/v MgSO$_4$.7H$_2$O
0.2% w/v MnSO$_4$.4H$_2$O
[b]Enzyme unit = mg./100 ml. reducing sugar (calculated as D-mannose) liberated per ml. broth in 1 hour at 42° C. and pH 5.4.

EXAMPLE 6

The effect on xanthanase production of substituting crude xanthan for the purified gum was determined on the following media.

| Nutrient | Inoculum medium % w/v | Test medium % w/v |
|---|---|---|
| crude xanthan liquor | 17.9[a] v/v | 17.9[a] v/v |
| (NH$_4$)$_2$SO$_4$ | 0.05 | 0.05 |
| yeast extract | 0.08 | — |
| tryptone | 0.04 | 0.18 |
| KH$_2$PO$_4$ | 0.07 | — |
| K$_2$HPO$_4$ | 0.15 | 0.20 |
| MgSO$_4$.7H$_2$O | 0.04 | 0.04 |
| MnSO$_4$.4H$_2$O | 0.002 | 0.002 |
| NaCl | 4.0 | 4.0 |
| pH | 6.0 | 6.3[b] |

[a]Equivalent to approximately 0.25% dry weight/volume.
[b]Adjusted from pH 6.9 with H$_2$SO$_4$.

A mixed culture for B-4529+strain 17 was built up on progressively increasing quantities of the inoculum medium. The test medium was made up to 7 l. with distilled water and was cooked in a fermentor for 20 minutes. After cooling, the medium was combined with 500 ml. of inoculum and made up to 10 l. with distilled water. The test medium having an initial pH of 6.15 was then fermented at 29° C. in a 20-l. fermentor aerated with 0.5 vol. air (5.0 l.)/minute and stirred at 200 r.p.m. After 3 days the final pH was 6.65 and the xanthanase activity was 205 enzyme units.

EXAMPLE 7

The combined broth from several fermentations similar to that described in Example 6 was assayed as having an enzyme activity of 210 units. The broth was centrifuged through a "Sharples" supercentrifuge to yield 89.4 l. of substantially cell-free supernatant which was concentrated in an "Amicon" DC-30 hollow fiber filtration assembly to about 10 l. in 3½ hours. Eight liters of cold distilled water was added and the total volume was reduced to about 4 l. Six liters of cold 0.05 M NaOAc buffer (pH 5.4) was added and the total volume reduced to about 4 l. by dialysis in the "Amicon" filtration assembly. Dialysis against the buffer was repeated resulting in removal of at least 90% of the NaCl. A final centrifugation yielded 3940 ml. of cell-free concentrate having an enzyme activity of 4943 units/ml. This corresponds to a specific acitivity of 1954 units/mg. protein.

EXAMPLE 8

Ten grams of xanthan gum was slurried in 150 ml. of NaOAc (0.05 M, pH 5.4) buffer. To this was added 50 ml. of the concentrated enzyme prepared by the procedure of Example 7 above. The mixture was incubated at 35°–37° C. in a 500-ml. shaker flask, and was preserved by the addition of 3–5 drops toluene daily. The results of xanthan degradation by the enzyme are reported in Table IX, below.

TABLE IX

| Day | Viscosity (cp.) | Conversion to sugar (% by wt.) |
|---|---|---|
| 0 | >20,000 | — |
| 3 | 551 | 28.6 |
| 4 | 274 | 33.8 |
| 6 | 96 | 41.0 |
| 7 | 67 | 41.4 |
| 10 | 44 | 42.0 |
| 12 | 30 | 43.4 |
| 14 | 27 | 44.0 |

EXAMPLE 9

Five grams of xanthan was slurried directly into 100 ml. of the concentrated xanthanase prepared by the procedure of Example 7. The mixture was incubated at 35° C. in a 300-ml. shaker flask, and was preserved by the addition of 6–8 drops of toluene. After 19 hours the slurry viscosity was reduced from an initial value exceeding 20,000 cp. to 48 cp. After 2 days, the viscosity was reduced to 30 cp. and the polysaccharide converted to sugar was 41.1% by weight.

EXAMPLE 10

A column packed with "Whatman DE 52" diethylaminoethyl cellulose was prepared with 0.05 M NaOAc buffer at pH 5.4 with 0.01% w/v $MgSO_4.7H_2O$ and 0.0005% w/v $MnSO_4.4H_2O$. Thirty milliliters of the concentrated enzyme solution prepared in Example 7 was placed on the column. The buffered salt solution was run through the column at a flow rate of 50 ml./hour and samples were taken at 15-minute intervals. The sample was then eluted with 0.5 M NaOAc/1 M NaCl using a 20-hour program. Tubes 67–82 were assayed as containing 85% of the active fraction. These tubes were combined and the resultant liquid had an activity of 124 enzyme units and a specific acitivity of 31,270 units/mg. of protein.

It is understood that the foregoing detailed description is given merely by way of illustration and that modification and variations may be made therein without departing from the spirit and scope of the invention.

I claim:

1. A method for degrading xanthan gum comprising fermenting said gum with a mixed culture comprising: (1) a first soil bacterium bearing the ARS Culture Collection Accession No. NRRL B-4529; and (2) at least one other soil bacterium capable of enhancing the growth of said first soil bacterium when in mixed culture therewith on a xanthan-containing medium; wherein the fermentation is conducted under aerobic conditions suitable for the growth of said first soil bacterium and for the elaboration of xanthanase by said first soil bacterium.

2. A method as described in claim 1 wherein said other soil bacterium is selected from the group of Arthrobacter, Alcaligenes, Agrobacterium, Brevibacterium, Flavobacterium, Micrococcus, and Xanthomonas.

3. A method as described in claim 1 wherein said other soil bacterium is selected from the group of *Arthrobacter globiformis, Arthrobacter simplex, Arthrobacter viscosus, Alcaligenes faecalis, Agrobacterium radiobacter, Brevibacterium linens, Flavobacterium aquatile,* Flavobacterium sp. NRRL B-14010, *Micrococcus luteus,* and *Xanthomonas campestris.*

4. A method as described in claim 1 wherein said other soil bacterium is Flavobacterium sp. NRRL B-14010.

5. A method for producing a salt-tolerant xanthanase comprising the following steps:
   a. culturing on a xanthan gum-containing medium a mixed culture comprising (1) a first soil bacterium bearing the ARS Culture Collection Accession No. NRRL B-4529, and (2) at least one other soil bacterium capable of enhancing the growth of said first soil bacterium when in mixed culture therewith on a xanthan-containing medium; wherein said fermentative culturing is conducted under aerobic conditions suitable for the growth of said first soil bacterium and for the elaboration of xanthanase by said first soil bacterium; and
   b. recovering said xanthanase from said medium.

6. A method as described in claim 5 wherein said other soil bacterium is selected from the group of Arthrobacter, Alcaligenes, Agrobacterium, Brevibacterium, Flavobacterium, Micrococcus, and Xanthomonas.

7. A method as described in claim 5 wherein said other soil bacterium is selected from the group of *Arthrobacter globiformis, Arthrobacter simplex, Arthrobacter viscosus, Alcaligenes faecalis, Agrobacterium radiobacter, Brevibacterium linens, Flavobacterium aquatile,* Flavobacterium sp. NRRL B-14010, *Micrococcus luteus,* and *Xanthomonas campestris.*

8. A method as described in claim 5 wherein said other soil bacterium is Flavobacterium sp. NRRL B-14010.

* * * * *